(12) United States Patent
Sakai (10) Patent No.: US 7,874,979 B2
(45) Date of Patent: Jan. 25, 2011

(54) OBSERVATION METHOD OF BIOLOGICAL TISSUE

(75) Inventor: Ikuko Sakai, Tachikawa (JP)

(73) Assignee: Olympus Corporation, Tokyo (JP)

( * ) Notice: Subject to any disclaimer, the term of this patent is extended or adjusted under 35 U.S.C. 154(b) by 957 days.

(21) Appl. No.: 11/730,073

(22) Filed: Mar. 29, 2007

(65) Prior Publication Data

US 2007/0238965 A1    Oct. 11, 2007

(30) Foreign Application Priority Data

Apr. 6, 2006    (JP) .............................. 2006-105591
Mar. 22, 2007    (JP) .............................. 2007-074971

(51) Int. Cl.
*A61B 1/00* (2006.01)
*A61B 19/00* (2006.01)

(52) U.S. Cl. ........................ 600/101; 600/102; 600/114; 128/898

(58) Field of Classification Search ................. 600/101, 600/102, 114, 183; 128/898, 897; 606/125, 606/213; 602/52
See application file for complete search history.

(56) References Cited

U.S. PATENT DOCUMENTS

| 4,929,246 A * | 5/1990 | Sinofsky ........................ 606/8 |
| 5,176,649 A * | 1/1993 | Wakabayashi ......... 604/164.09 |
| 6,726,696 B1 * | 4/2004 | Houser et al. ................ 606/151 |
| 2001/0047135 A1 * | 11/2001 | Daniels et al. ............... 600/466 |
| 2005/0094260 A1 | 5/2005 | Tokuda et al. |

FOREIGN PATENT DOCUMENTS

JP    2005-253836    9/2005

* cited by examiner

*Primary Examiner*—John P Leubecker
(74) *Attorney, Agent, or Firm*—Pillsbury Winthrop Shaw Pittman, LLP (57) ABSTRACT

When an observation target in a membranous tissue such as an amniotic membrane filled with a liquid such as an amniotic fluid is observed, the observation is performed without leaking the liquid. There is provided an observation method of an observation target arranged in a membranous tissue filled with a body fluid, comprising: a step for coating a gel-like adhesive on the outer surface of the membranous tissue; a step for cutting the membranous tissue through the coated adhesive; a step for inserting the distal end of the objective unit through the adhesive and the open cut in the membranous tissue; and a step for observing the observation target through the inserted distal end of the objective unit.

3 Claims, 7 Drawing Sheets

OBSERVATION METHOD OF BIOLOGICAL TISSUE

BACKGROUND OF THE INVENTION

1. Field of the Invention

The present invention relates to an observation method for observing a biological tissue in a living state (in vivo).

This application is based upon and claims the benefit of priority from Japanese Patent Application No. 2006-105591, filed on Apr. 6, 2006, and Japanese Patent Application No. 2007-74971, filed on Mar. 22, 2007, the entire contents of these applications are incorporated herein by reference.

2. Description of Related Art

Conventionally, as this kind of observation method, for example, an observation method disclosed in Japanese Unexamined Patent Application, Publication No. 2005-253836, is known.

In this observation method, an objective optical unit which stores an objective optical system in an outer sheath is supported in a hole formed in a biological tissue in an inserted state by a supporting member, to fix the supporting member to the biological tissue, and thereby the same observation target site in the marrow can be observed with a high reproducibility by inserting and withdrawing the objective optical unit through the supporting member.

However, in the observation method disclosed in Japanese Unexamined Patent Application, Publication No. 2005-253836, no case is disclosed where an observation target which is within an internal area defined by a membranous tissue or the like filled with a body fluid is observed.

That is, for example, the inside of the amniotic membrane is filled with the amniotic fluid, and if a fetus exists inside thereof, the objective optical unit has to be inserted through the amniotic membrane. Moreover, after a through hole is formed in the amniotic membrane and the observation is completed, and after the objective optical unit is withdrawn, the amniotic fluid has to be continuously held in the amniotic membrane.

However, if the amniotic membrane simply passes through by the distal end of the objective optical unit, there is a disadvantage in that the internal amniotic fluid leaks out due to the internal pressure inside the amniotic membrane, and the observation target such as the fetus floating in the amniotic fluid in a healthy state can not be observed. Moreover, there is a disadvantage in that, after a through hole is formed in the amniotic membrane and the observation is completed, when the objective optical unit is withdrawn, the internal amniotic fluid leaks out due to the internal pressure inside the amniotic membrane, and thereby the amniotic fluid can not be continuously held in the amniotic membrane.

BRIEF SUMMARY OF THE INVENTION

The present invention takes the above problems into consideration, with the object of providing an observation method in which, when an observation target in a membranous tissue such as an amniotic membrane filled with a liquid such as an amniotic fluid is observed, the observation can be performed without leaking the liquid. Moreover, another object is to provide an observation method in which, after the observation, even if the objective unit is taken out, the liquid can be held in the membranous tissue without leaking, and the health of the internal observation target can be maintained.

In order to achieve the above object, the present invention provides the following solutions.

The present invention provides an observation method of an observation target arranged in a membranous tissue filled with a body fluid, comprising: a step for coating a gel-like adhesive on the outer surface of the membranous tissue; a step for cutting the membranous tissue through the coated adhesive; a step for inserting the distal end of the objective unit through the adhesive and the open cut in the membranous tissue; and a step for observing the observation target through the inserted distal end of the objective unit.

According to the present invention, since the membranous tissue is cut through the gel-like adhesive coated in the step for coating the adhesive, the adhesive seals around a cutting member, and the liquid in the membranous tissue is prevented from leaking out. Moreover, since the distal end of the objective unit is also inserted into the membranous tissue through the open cut coated with the adhesive, around the objective unit is sealed by the adhesive, and the liquid in the membranous tissue is prevented from leaking out.

In this state, by operating the objective unit, the observation target in the membranous tissue can be observed through the distal end. As a result, even in the observation state, around the objective unit is sealed by the adhesive and the liquid in the membranous tissue can be prevented from leaking out.

Furthermore, after the observation, even if the objective unit is withdrawn from the open cut in the membranous tissue, the gel-like adhesive seals the open cut, and thereby the liquid in the membranous tissue can be prevented from leaking out.

In the above invention, the adhesive is preferably transparent.

When the distal end of the objective unit is inserted into the membranous tissue through the adhesive, even if the adhesive is adhered onto the distal end of the objective unit, as long as the adhesive is transparent, the field of vision is not blocked and the observation target can be observed.

In the above invention, a marking member may be provided on the distal end of the objective unit, and a step for applying a marker to the observed site on the observation target may be further provided.

By so doing, since the marker is applied to the observed site on the observation target, even in a continuous observation where the distal end of the objective unit is inserted and withdrawn, the already observed site can be ensured using the marker as a guide, and the observation can be readily performed at the same site or a site different from the already observed site.

According to the present invention, an effect is demonstrated in which, when an observation target in a membranous tissue such as an amniotic membrane filled with a liquid such as an amniotic fluid is observed, the observation can be performed without leaking the liquid. Moreover, an effect is demonstrated in which, after the observation, even if the objective unit is taken out, the liquid can be held in the membranous tissue without leaking, and the health of the internal observation target can be maintained.

DETAILED DESCRIPTION OF THE INVENTION

Hereunder is a description of the observation method according to an embodiment of the present invention, with reference to FIG. 1 to FIG. 7.

Figure 1:
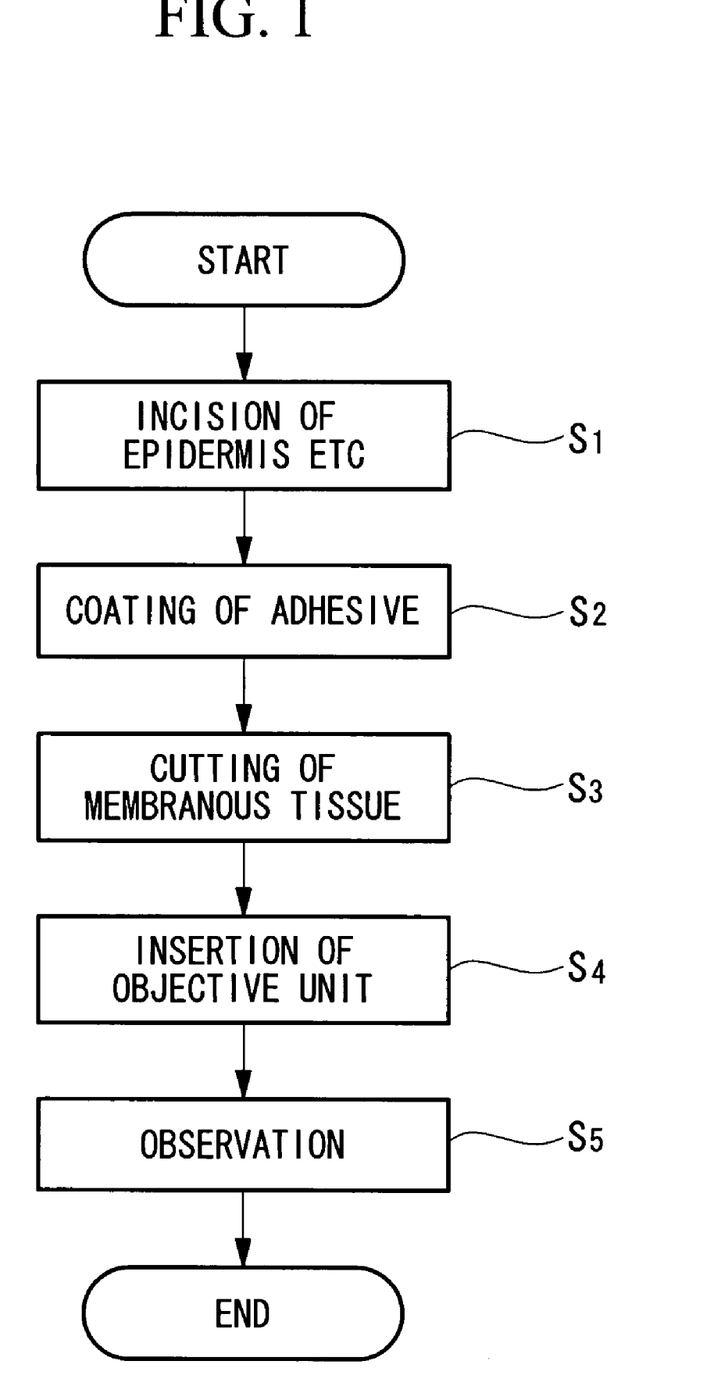
FIG. 1 is a flowchart describing the observation method according to an embodiment of the present invention.
Figure 2:
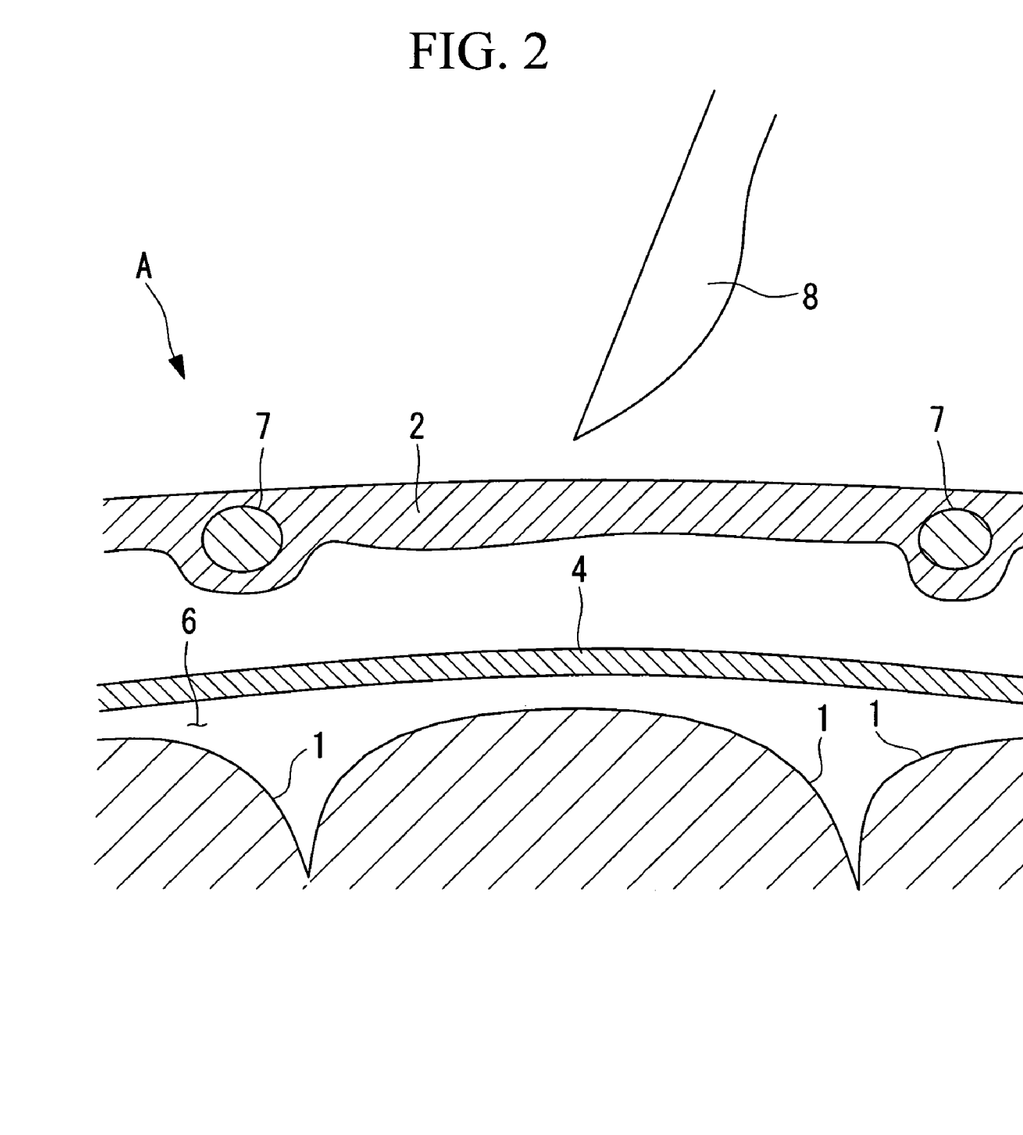
FIG. 2 illustrates a step for incising the epidermis, in the observation method of FIG. 1.

The observation method according to the present embodiment is a method for observing, for example, a fetus (observation target) 1 of a mouse A in a living state, comprising: as shown in FIG. 1 to FIG. 7, a step $S_1$ for incising the epidermis 2 and the like; a step $S_2$ for coating an adhesive 3; a step $S_3$ for cutting the amniotic membrane (membranous tissue) 4; a step $S_4$ for inserting an objective unit 5; and a step $S_5$ for observing the fetus 1. As shown in FIG. 2, the fetus 1 of the mouse A is arranged in the uterine fascia and the amniotic membrane 4 filled with the amniotic fluid (body fluid) 6.

As shown in FIG. 2, in step $S_1$ for incising the epidermis 2 and the like, the epidermis 2 and the muscular tissue arranged between the ribs 7 of the mouse A are cut and opened by a cutting instrument 8 such as a scalpel. As a result, the amniotic membrane 4 arranged inside of the epidermis 2 and the muscular tissue is exposed.

Figure 3:
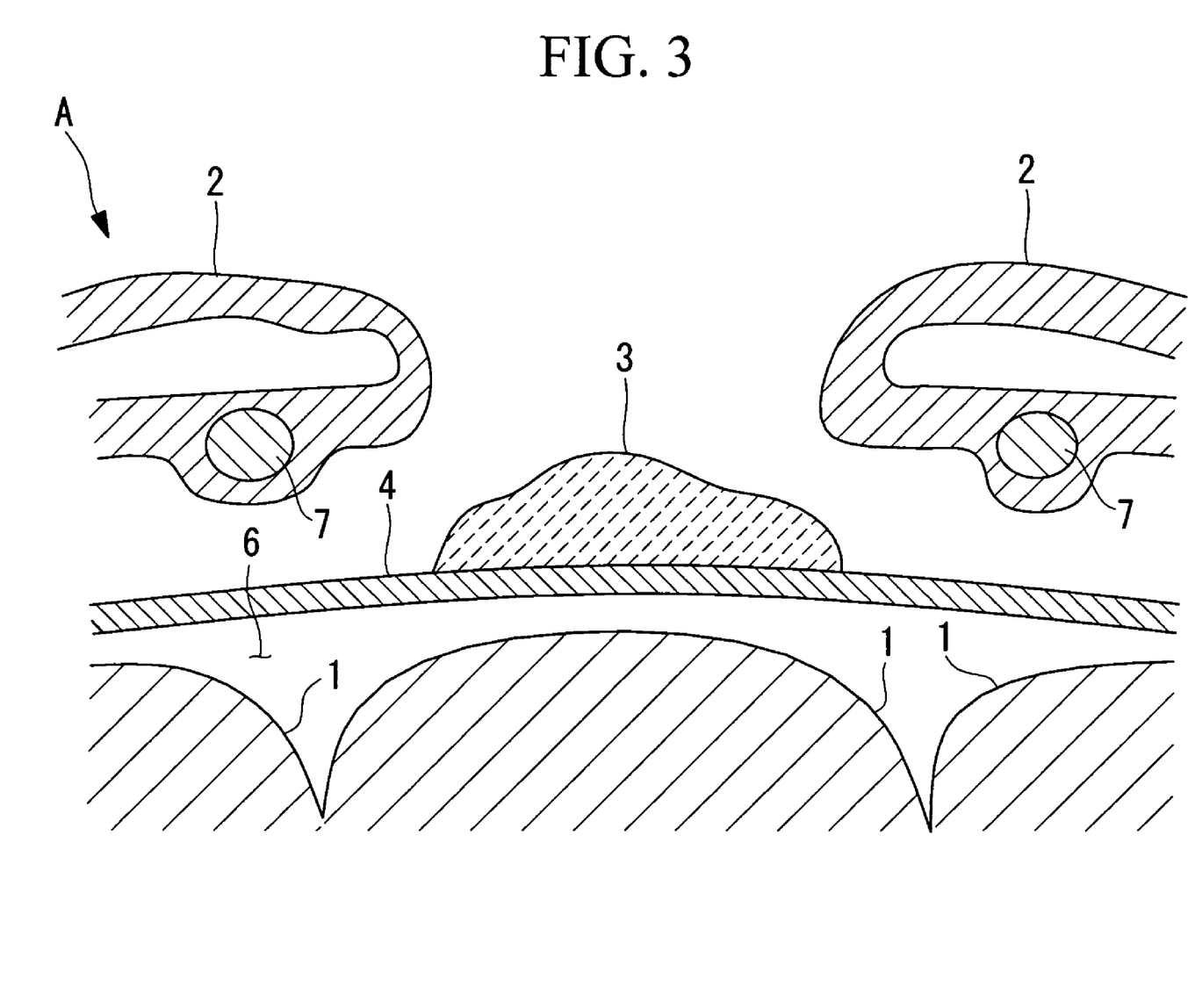
FIG. 3 illustrates a step for coating an adhesive, in the observation method of FIG. 1.

As shown in FIG. 3, in step $S_2$ for coating an adhesive, a gel-like adhesive 3 is heaped on the outer surface of the amniotic membrane 4 that has been exposed in step $S_1$. The gel-like adhesive 3 is a biocompatible adhesive 3. For example, adhesives 3 of fibrin type, gelatin type, GTXIII type, cyanoacrylate type, urethane type, collagen type, chitin type, or stimulation responsive gel protein type, or those mixed with elastin to adjust the elasticity, are used.

The adhesive 3 is not limited to these, and any arbitrary biocompatible adhesive 3 may be used.

Moreover, for the adhesive 3, an adhesive 3 of a transparent material is preferably used.

Figure 4:
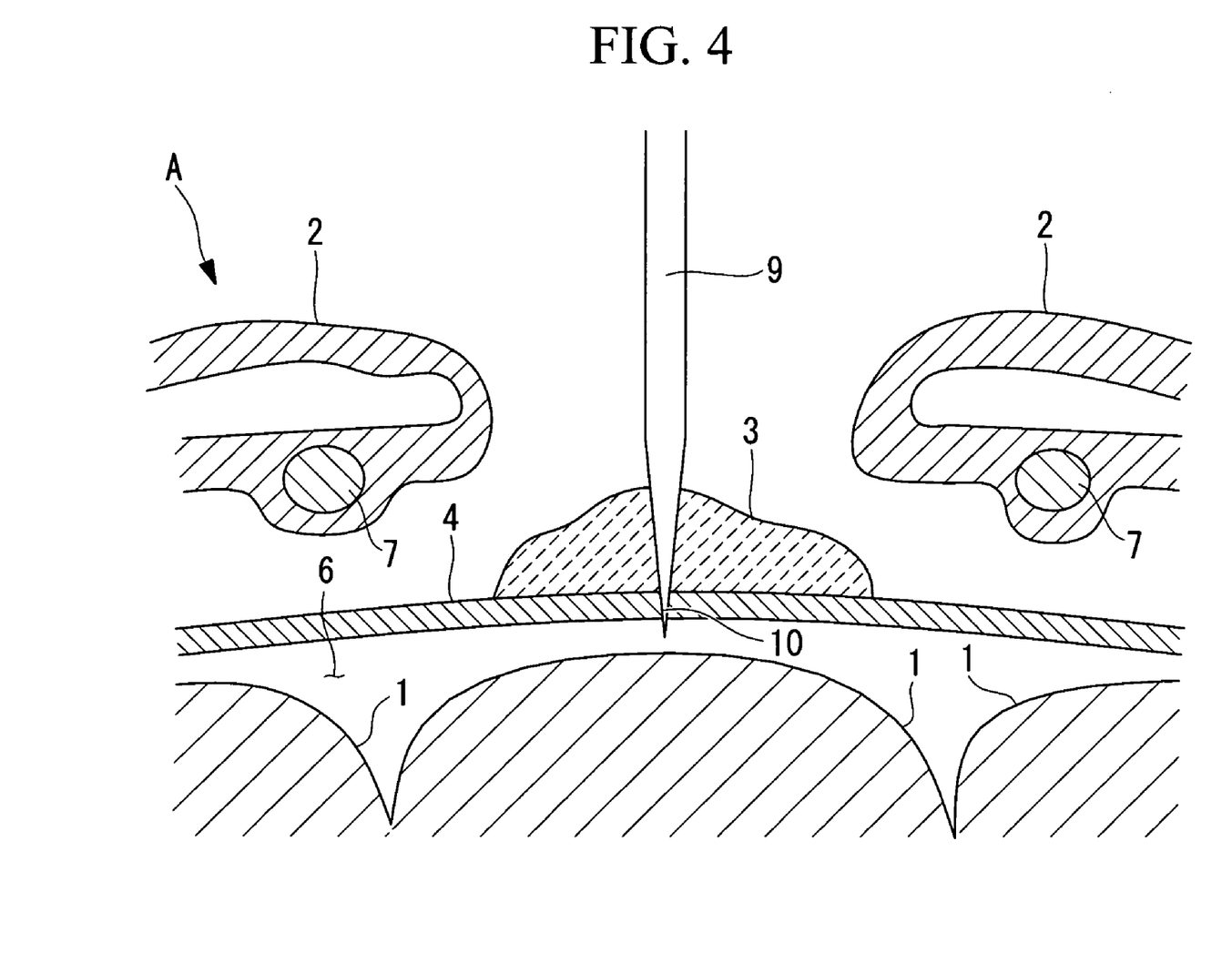
FIG. 4 illustrates a step for cutting the membranous tissue, in the observation method of FIG. 1.

As shown in FIG. 4, in step $S_3$ for cutting the amniotic membrane 4, a boring instrument 9 having a scalpel or other sharp edge passes through the adhesive 3 that has been coated in step $S_2$, to form an open cut 10 in the amniotic membrane 4 in the area coated with the adhesive 3. Since the space in the amniotic membrane 4 is filled with the amniotic fluid 6 and has a predetermined internal pressure, at the instant when the boring instrument 9 passes through the amniotic membrane 4, the amniotic fluid 6 is to be ejected from the amniotic membrane 4. However, in the present embodiment, since around the boring instrument 9 is enclosed and sealed by the gel-like adhesive 3, the amniotic fluid 6 does not leak out to the outside.

Figure 5:
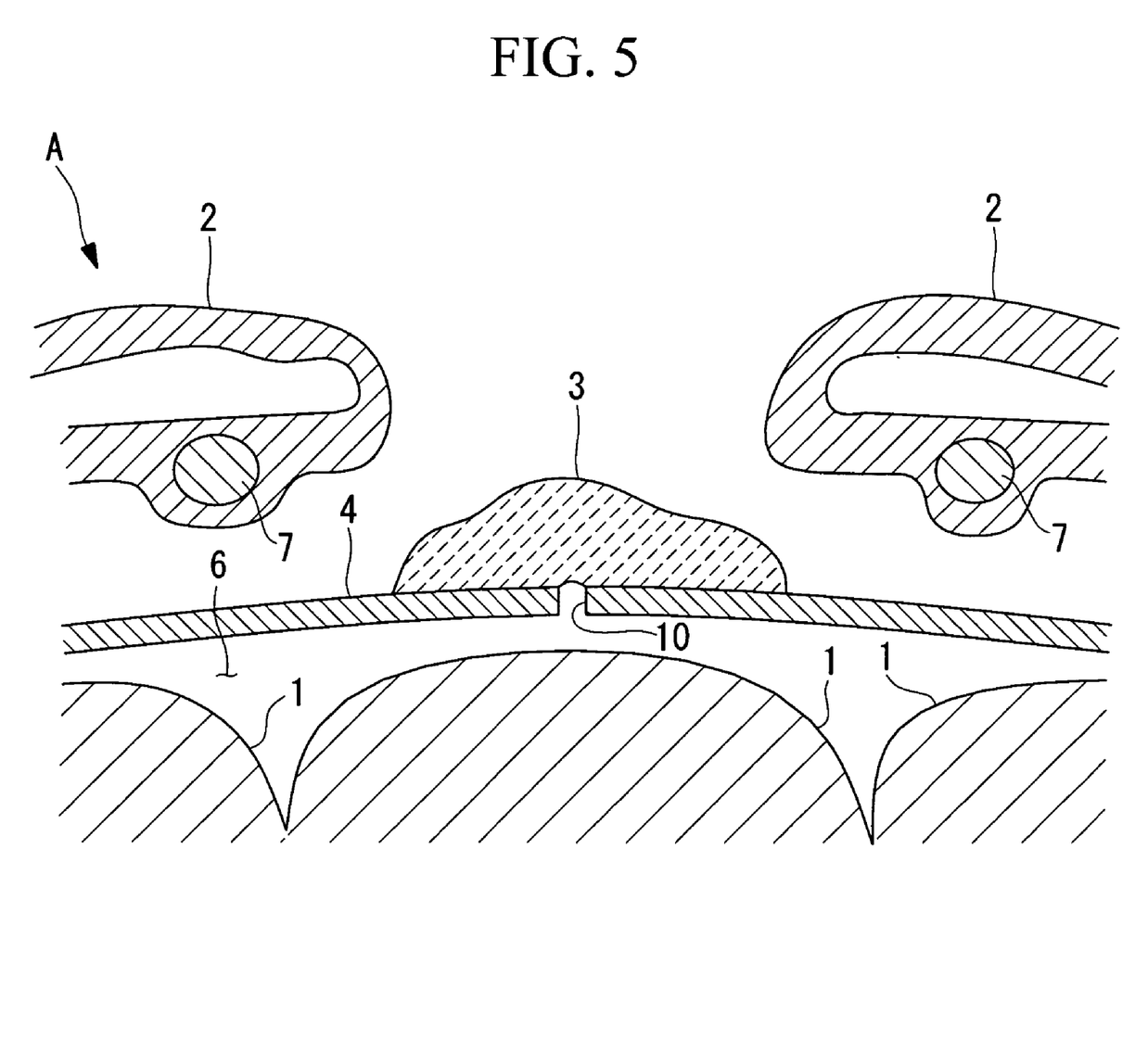
FIG. 5 illustrates a state where an open cut is formed in the membranous tissue, in the observation method of FIG. 1.

Moreover, as shown in FIG. 5, after cutting of the amniotic membrane 4 is completed and the open cut 10 is formed in the amniotic membrane 4, even if the boring instrument 9 is withdrawn, the adhesive 3 sealing around the boring instrument 9 sequentially blocks the track through which the boring instrument 9 passed, and thereby the amniotic fluid 6 is held so as not to leak out to the outside.

Figure 6:
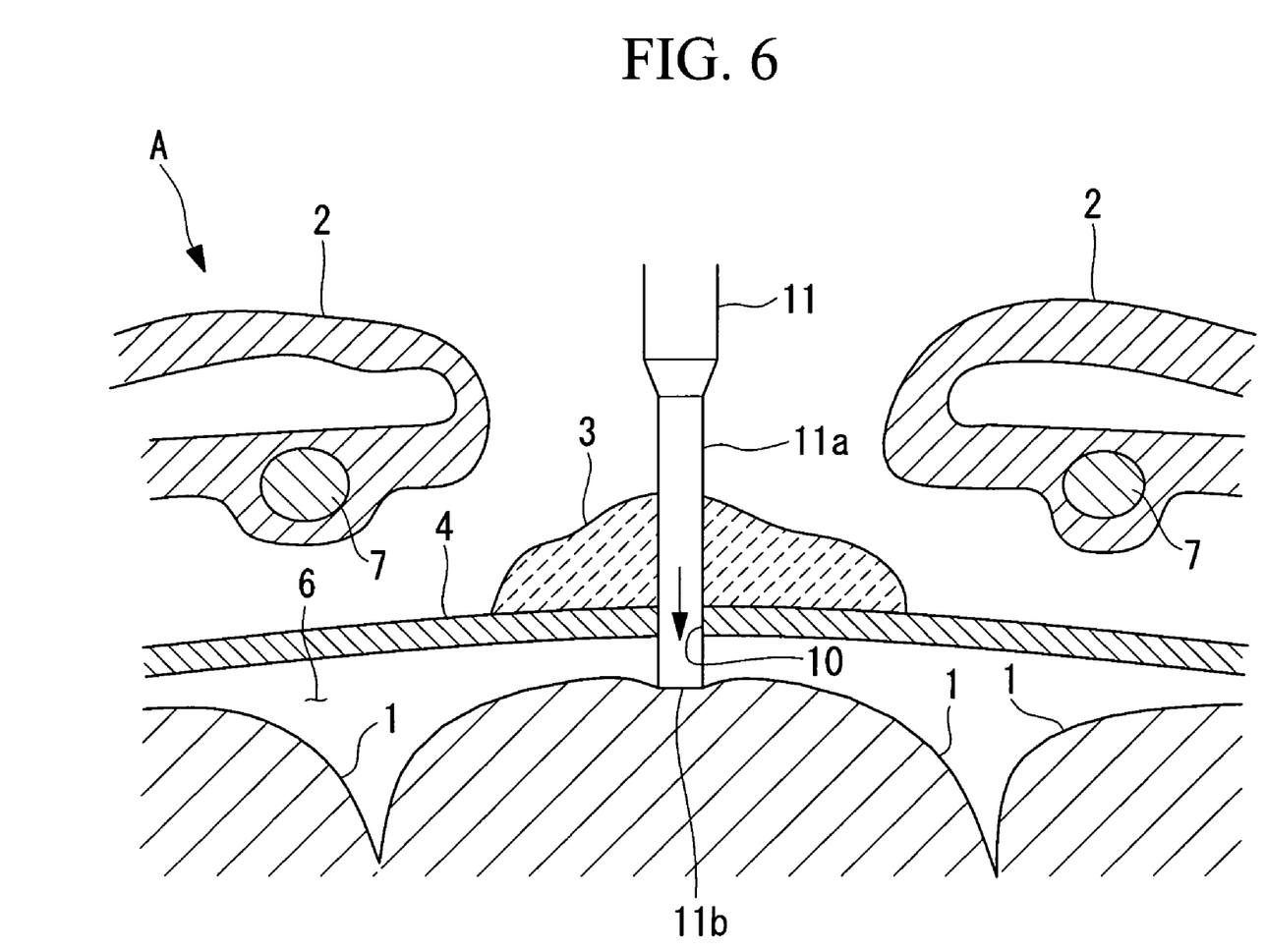
FIG. 6 illustrates a step for inserting an objective unit and observing, in the observation method of FIG. 1.

As shown in FIG. 6, in step $S_4$ for inserting the objective unit 11, the small diameter distal end 11a of the objective unit 11 is inserted into the amniotic membrane 4 through the open cut 10 formed in the step $S_3$. The objective unit 11 is attached to a microscopic observation device (not shown) and is designed such that illumination light such as exciting light like laser beams is irradiated from the distal end face 11b, and light such as fluorescence returning from the fetus 1 is collected.

In this step $S_4$, the small diameter distal end 11a of the objective unit 11 passes through the adhesive 3 coated on the outer surface of the amniotic membrane 4, reaches the open cut 10 formed in step $S_3$, and is inserted into the amniotic membrane 4 through the open cut 10. As a result, since around the small diameter distal end 11a of the objective unit 11 is sealed by the adhesive 3, the amniotic fluid 6 in the amniotic membrane 4 is held so as not to leak out to the outside even when the objective unit 11 is being inserted.

In step $S_5$ for observing the fetus 1, the distal end face 11b of the small diameter distal end 11a of the objective unit 11 that has been inserted into the amniotic fluid 6 is abutted against the outer surface of the fetus 1 serving as the observation target, so as to be stuck thereto, then exciting light is irradiated from the distal end face 11b, and fluorescence generated at the fetus 1 is collected. As a result, a fluorescent image of the fetus 1 can be obtained.

In this case, even during the observation of the fetus 1, around the small diameter distal end 11a of the objective unit 11 is sealed by the adhesive 3, and therefore the amniotic fluid 6 in the amniotic membrane 4 is held so as not to leak out to the outside.

Moreover, according to the present embodiment, since the transparent adhesive 3 is employed as the adhesive 3, even if the adhesive 3 is adhered onto the distal end face 11b of the objective unit 11 that has passed through the heaped adhesive 3, irradiation of exciting light and collection of fluorescence can be performed without much interference.

Figure 7:
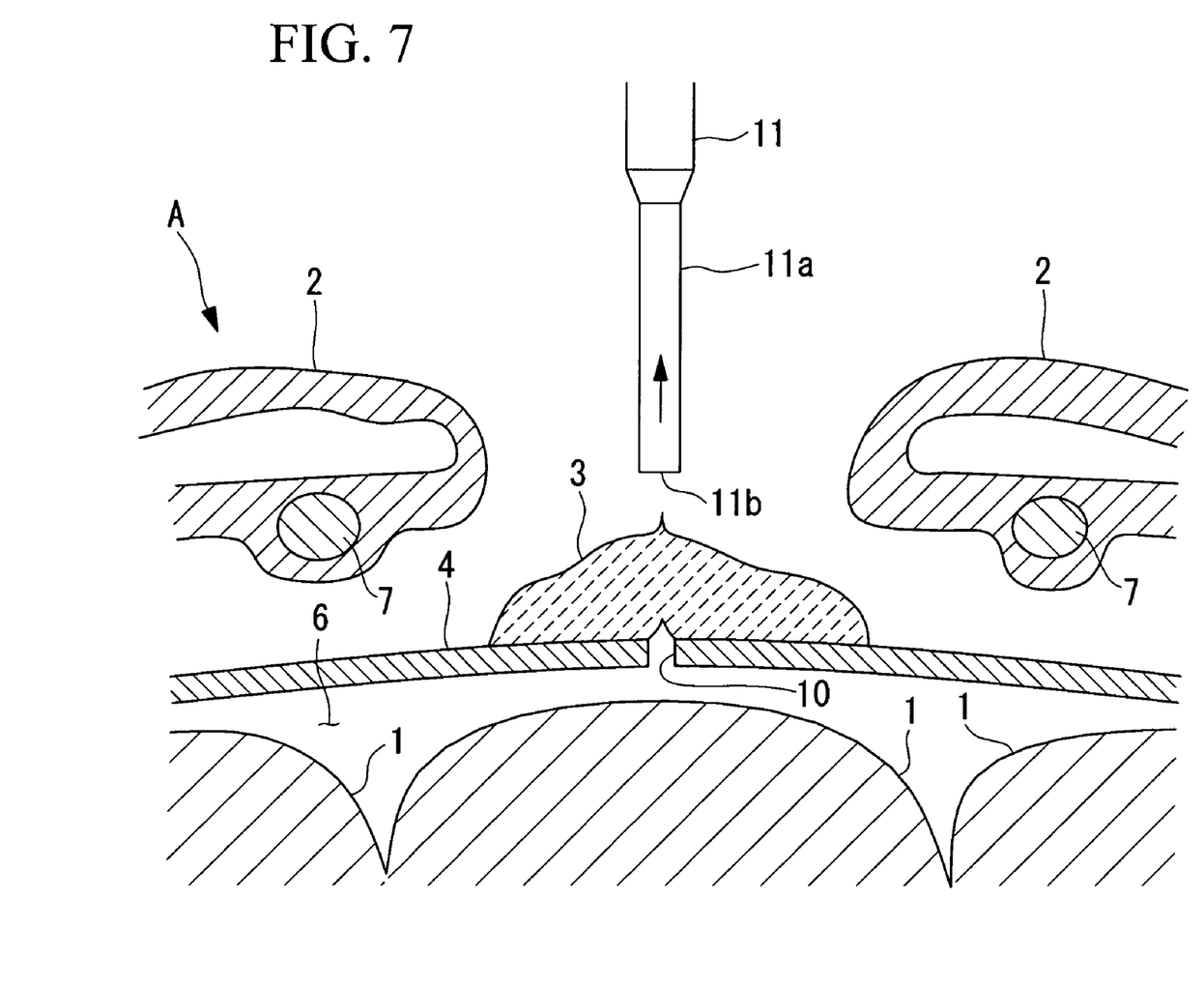
FIG. 7 illustrates a state where the objective unit is withdrawn after the observation, in the observation method of FIG. 1.

Furthermore, after the observation is completed, as shown in FIG. 7, the small diameter distal end 11a of the objective unit 11 is withdrawn from the open cut 10 in the amniotic membrane 4. In this case, the adhesive 3 sealing around the small diameter distal end 11a of the objective unit 11 sequentially blocks the track through which the small diameter distal end 11a passed, and thereby the amniotic fluid 6 is held so as not to leak out to the outside. Consequently, even after the observation, the amniotic fluid 6 can be held so as not to leak out to the outside, and the health of the observation target such as the fetus 1 in the amniotic fluid 6 can be maintained.

In this manner, according to the observation method according to the present embodiment, when an observation target such as the fetus 1 in the amniotic membrane 4 is observed, the observation can be performed without leaking the amniotic fluid 6 to the outside. Therefore, there is an advantage in that the fetus 1 can be observed in a living and healthy state.

Moreover, after the observation, even if the objective unit 11 is taken out, the amniotic fluid 6 can be held in the amniotic membrane 4 without leaking. Therefore, even after the observation, the health of the fetus 1 can be maintained. As a result, even if the objective unit 11 is repeatedly inserted and withdrawn for a plurality of times with time intervals, the health of the fetus 1 can be maintained and the observation can be performed in a living state over time.

In the observation method according to the present embodiment, the description is about the example where the method is applied to the case where the fetus 1 of the mouse A is observed, however it is not to be considered as limiting. The method may be applied to the case where an observation target existing in a membranous tissue filled with another arbitrary liquid is observed.

Moreover, the amniotic membrane 4 is cut by the boring instrument 9, and then the objective unit 11 is inserted thereinto. However, instead, as long as a sharp cutting blade can be arranged at the distal end of the objective unit 11, the amniotic membrane 4 can be bored at the same time when the objective unit 11 is inserted.

Furthermore, the description is about the case where the objective unit 11 is repeatedly inserted and withdrawn for a plurality of times with time intervals to perform the observation over time. In this case, a marking member that applies an arbitrary marker such as a tracer protein to the observation target, may be used. By so doing, the marker can be applied to the already observed site, and the next observation can be readily performed at the same site or a different site. The marking member is preferably provided to the small diameter distal end 11a of the objective unit 11.

Moreover, as the objective unit 11, a hard mirror type having the small diameter distal end 11a was exemplified, however it is not to be considered as limiting. For example, a fiber bundle or the like may be used.

What is claimed is:

1. An observation method of an observation target arranged in a membranous tissue filled with a body fluid, comprising:
    a step for coating a gel-like adhesive on an outer surface of the membranous tissue;
    a step for cutting the membranous tissue through the coated adhesive;
    a step for inserting a distal end of the objective unit through the adhesive and an open cut in the membranous tissue; and
    a step for observing the observation target through the inserted distal end of the objective unit.

2. An observation method according to claim 1, wherein the adhesive is transparent.

3. An observation method according to claim 1, wherein there is further provided a step for applying a marker to the observed site on the observation target by a marking member provided on the distal end of the objective unit.

* * * * *